United States Patent
Biegert et al.

(10) Patent No.: US 9,754,076 B2
(45) Date of Patent: Sep. 5, 2017

(54) IDENTIFYING ERRORS IN MEDICAL DATA

(71) Applicant: International Business Machines Corporation, Armonk, NY (US)

(72) Inventors: Keith P. Biegert, Cary, NC (US); Brendan C. Bull, Durham, NC (US); David Contreras, Apex, NC (US); Robert C. Sizemore, Fuquay-Varina, NC (US); Sterling R. Smith, Apex, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/860,834

(22) Filed: Sep. 22, 2015

(65) Prior Publication Data
US 2017/0024887 A1    Jan. 26, 2017

Related U.S. Application Data

(63) Continuation of application No. 14/806,746, filed on Jul. 23, 2015.

(51) Int. Cl.
*G06K 9/00* (2006.01)
*G06F 19/00* (2011.01)
(Continued)

(52) U.S. Cl.
CPC .......... *G06F 19/322* (2013.01); *G06F 17/271* (2013.01); *G06F 17/2765* (2013.01); *G06F 17/2785* (2013.01); *G06F 17/28* (2013.01); *G06F 17/30253* (2013.01); *G06F 17/30401* (2013.01); *G06K 9/00442* (2013.01); *G06K 9/6201* (2013.01); *G06K 9/72* (2013.01);
(Continued)

(58) Field of Classification Search
None
See application file for complete search history.

(56) References Cited

U.S. PATENT DOCUMENTS

| 7,668,376 B2 | 2/2010 | Lin et al. | |
|---|---|---|---|
| 2001/0031088 A1* | 10/2001 | Natori | G06K 9/723 382/229 |

(Continued)

FOREIGN PATENT DOCUMENTS

| CN | 103631953 A | 3/2014 |
|---|---|---|
| CN | 104520862 A | 4/2015 |

(Continued)

OTHER PUBLICATIONS

List of IBM Patents or Patent Applications Treated as Related, dated Sep. 18, 2015, pp. 1-2.

(Continued)

*Primary Examiner* — Hadi Akhavannik
(74) *Attorney, Agent, or Firm* — Robert J. Shatto

(57) ABSTRACT

A computer processor may receive medical data including a report and an image. The computer processor may analyze the report using natural language processing to identify a condition and a corresponding criterion. The computer processor may also analyze the image using an image processing model to generate an image analysis. The computer processor may determine whether the report has a potential problem by comparing the image analysis to the criterion.

17 Claims, 4 Drawing Sheets

(51) Int. Cl.
  *G06F 17/30* (2006.01)
  *G06F 17/27* (2006.01)
  *G06F 17/28* (2006.01)
  *G06K 9/62* (2006.01)
  *G06T 7/00* (2017.01)
  *G06K 9/72* (2006.01)

(52) U.S. Cl.
  CPC .......... *G06T 7/0014* (2013.01); *G06K 9/6293* (2013.01); *G06K 2209/01* (2013.01); *G06K 2209/05* (2013.01)

(56) References Cited

U.S. PATENT DOCUMENTS

| | | | | |
|---|---|---|---|---|
| 2002/0064316 | A1* | 5/2002 | Takaoka | G06F 17/2872 382/305 |
| 2004/0103367 | A1* | 5/2004 | Riss | G06F 17/2264 715/223 |
| 2006/0007188 | A1* | 1/2006 | Reiner | G06F 3/04883 345/179 |
| 2006/0285749 | A1* | 12/2006 | Eisenhart | G06K 9/00402 382/188 |
| 2007/0098298 | A1 | 5/2007 | Xiang | |
| 2007/0237378 | A1* | 10/2007 | Reiner | G06F 3/04883 382/128 |
| 2008/0267473 | A1 | 10/2008 | Wang et al. | |
| 2009/0192822 | A1* | 7/2009 | Regulapati | G06F 19/325 705/3 |
| 2010/0114597 | A1* | 5/2010 | Shreiber | G06F 19/321 705/2 |
| 2011/0075901 | A1* | 3/2011 | Nakamura | G06F 19/321 382/128 |
| 2012/0173524 | A1* | 7/2012 | Connor | G06Q 10/10 707/736 |
| 2012/0183188 | A1* | 7/2012 | Moriya | G06F 19/321 382/128 |
| 2012/0189175 | A1 | 7/2012 | Highnam et al. | |
| 2012/0219175 | A1 | 8/2012 | Richardson et al. | |
| 2014/0064592 | A1 | 3/2014 | Nortmann et al. | |
| 2014/0072192 | A1* | 3/2014 | Reiner | G06T 7/0012 382/128 |
| 2015/0104087 | A1 | 4/2015 | Katuwal et al. | |
| 2017/0024517 | A1 | 1/2017 | Biegert et al. | |

FOREIGN PATENT DOCUMENTS

| | | |
|---|---|---|
| WO | 9803933 A1 | 1/1998 |
| WO | 2004066842 A1 | 8/2004 |
| WO | 2008131459 A1 | 10/2008 |
| WO | 2017013518 A1 | 1/2017 |

OTHER PUBLICATIONS

International Search Report, International Application No. PCT/IB2016/054023, Jul. 5, 2016, 7 pgs.

Written Opinion, International Application No. PCT/IB2016/054023, Oct. 11, 2016, 4 pgs.

Voll, "A Methodology of Error Detection: Improving Speech Recognition in Radiology," Thesis for B.A., Simon Fraser University, Spring 2006, 208 pages.

* cited by examiner

US 9,754,076 B2

IDENTIFYING ERRORS IN MEDICAL DATA

BACKGROUND

The present disclosure relates generally to the field of natural language processing, and more particularly to using natural language processing and image analysis to identify errors in medical data.

When a doctor diagnoses a patient with a medical condition, such as a bone fracture, the doctor often writes a medical report detailing the condition and key information about the condition, such as its severity. For example, a radiologist might note the size and type of a bone fracture from his analysis of an X-Ray image. These medical reports may then be sent, along with any medical images taken of the patient, to third parties who need the report to further the patient's care. For example, the medical report and X-Ray images may be sent to another doctor who is going to treat the patient, such as a surgeon. The medical report and images may also be sent to an insurance company to request approval of a claim or procedure.

SUMMARY

Embodiments of the present invention disclose a computer implemented method for identifying errors in medical data. A computer processor may receive medical data including a report and an image. The computer processor may analyze the report using natural language processing to identify a condition and a corresponding criterion. The computer processor may also analyze the image using an image processing model to generate an image analysis. The computer processor may determine whether the report has a potential problem by comparing the image analysis to the criterion.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of typical embodiments and do not limit the disclosure.

Figure 1:
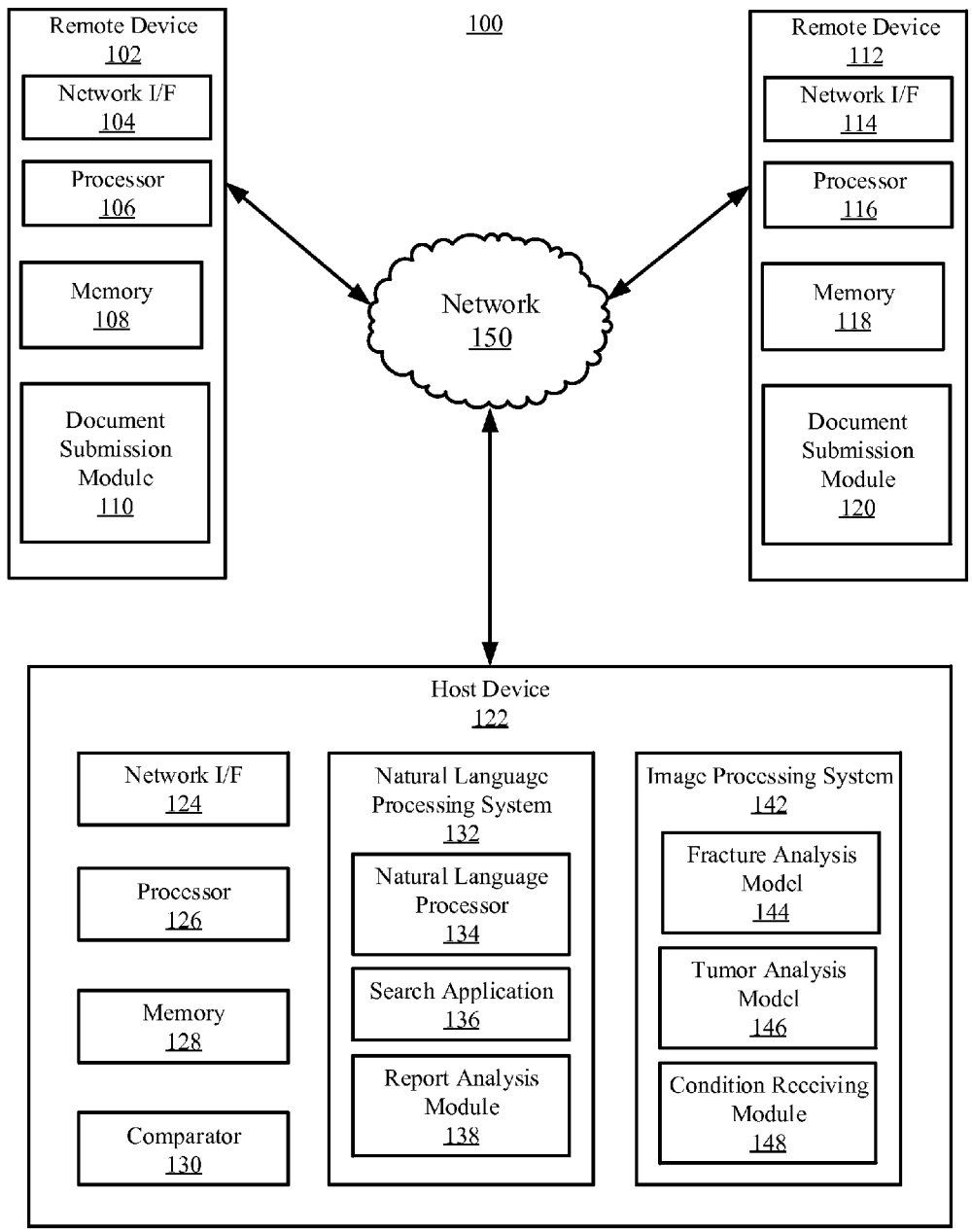
FIG. 1 illustrates a block diagram of an example computing environment in which illustrative embodiments of the present disclosure may be implemented.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the invention.

DETAILED DESCRIPTION

Aspects of the present disclosure relate generally to the field of natural language processing, and in particular to using natural language processing and image analysis to identify errors in medical data. While the present disclosure is not necessarily limited to such applications, various aspects of the disclosure may be appreciated through a discussion of various examples using this context.

When a doctor diagnoses a patient with a medical condition (hereinafter referred to as a condition), such as a bone fracture, the doctor often writes a medical report detailing the condition and key information about the condition, such as its severity. For example, a radiologist might note the size and type of a bone fracture (e.g., open, closed, transverse, spiral, hairline, etc.) from his analysis of an X-Ray image. These medical reports may then be sent, along with any corresponding medical images taken of the patient, to third parties who need the report to further the patient's care. For example, the medical report and X-Ray images may be sent to another doctor who is going to treat the patient, such as an orthopedic surgeon. The medical report and images may also be sent to an insurance company to request approval of a claim or procedure.

The third party that receives the medical report (or the individual sending the report) often uses optical character recognition (OCR), or a related process such as optical word recognition, intelligent character recognition (ICR), or intelligent word recognition (IWR), to convert the medical report into machine-encoded text. This may be done to make it easier to archive the report, to enter the contents of the report into a form (especially if done by a computer), and to make the report searchable by a computer.

OCR and related technologies are prone to making mistakes when converting an image into machine-encoded text, particularly when converting hand-written text. For example, OCR processes may read a "7" as a "1" (or vice versa). OCR is also prone to dropping characters, so that a 10 cm bone fracture may be reported as a 1 cm bone fracture. These errors often cause unnecessary delay in a patient's treatment. For example, an insurance company that believes a patient to have a 1 cm hairline fracture (instead of the actual 10 cm hairline fracture that the patient actually has) may deny a requested surgical procedure because the procedure is only appropriate for hairline fractures that are 5 cm or more in length. Other causes of errors in medical reports that may affect treatment of the patient include clerical errors, such as errors introduced when copying or transcribing the medical report.

In some embodiments, a computer system may analyze the medical report and accompanying images to identify potential errors in the medical report and to expedite the treatment of patients. The computer system may identify a condition and a criterion associated with the condition by analyzing the report. As used herein, a "criterion" refers to diagnostic information about a condition, such as the type and severity of the condition. For example, if the condition is a bone fracture, the associated criterion may indicate that the fracture is an "open" fracture. The computer system may also generate an image analysis by analyzing the medical images, such as X-Ray images. The image analysis may include an "image condition" (i.e., a medical condition identified in the image) and/or an "image criterion" (i.e., a criterion identified in the image). The computer system may then compare the condition and/or criterion identified in the report to the image analysis to determine whether there is a potential problem with the medical report. In some embodiments, if a potential problem with the report is discovered, the computer system may alert a user of the potential problem's existence.

In some situations, the computer system may analyze the medical report by searching for keywords in the report. The keywords may be selected from, e.g., a list of known conditions. This may be an unacceptable solution, however, as such a search may not take into consideration the context of the keyword in the medical report. Additionally, this solution may not be able to appropriately link a condition with its associated criterion, especially when the report includes multiple conditions and criteria. In some embodiments, natural language processing may be used to analyze the report in order to determine the condition and related criterion.

As discussed above, aspects of the disclosure may relate to natural language processing. Accordingly, an understanding of the embodiments of the present invention may be aided by describing embodiments of natural language processing systems and the environments in which these systems may operate. Turning now to the figures, FIG. 1 illustrates a block diagram of an example computing environment 100 in which illustrative embodiments of the present disclosure may be implemented. In some embodiments, the computing environment 100 may include two remote devices 102 and 112 and a host device 122.

Consistent with various embodiments, the host device 122 and the remote devices 102 and 112 may be computer systems. The remote devices 102 and 112 and the host device 122 may include one or more processors 106, 116, and 126 and one or more memories 108, 118, and 128, respectively. The remote devices 102 and 112 and the host device 122 may be configured to communicate with each other through an internal or external network interface 104, 114, and 124. The network interfaces 104, 114, and 124 may be, e.g., modems or network interface cards. The remote devices 102 and 112 and/or the host device 122 may be equipped with a display or monitor. Additionally, the remote devices 102 and 112 and/or the host device 122 may include optional input devices (e.g., a keyboard, mouse, scanner, or other input device), and/or any commercially available or custom software (e.g., browser software, communications software, server software, natural language processing software, search engine and/or web crawling software, filter modules for filtering content based upon predefined parameters, etc.). In some embodiments, the remote devices 102 and 112 and/or the host device 122 may be servers, desktops, laptops, or hand-held devices.

The remote devices 102 and 112 and the host device 122 may be distant from each other and communicate over a network 150. In some embodiments, the host device 122 may be a central hub from which remote devices 102 and 112 can establish a communication connection, such as in a client-server networking model. Alternatively, the host device 112 and remote devices 102 and 112 may be configured in any other suitable networking relationship (e.g., in a peer-to-peer configuration or using any other network topology).

In some embodiments, the network 150 can be implemented using any number of any suitable communications media. For example, the network 150 may be a wide area network (WAN), a local area network (LAN), an internet, or an intranet. In certain embodiments, the remote devices 102 and 112 and the host device 122 may be local to each other, and communicate via any appropriate local communication medium. For example, the remote devices 102 and 112 and the host device 122 may communicate using a local area network (LAN), one or more hardwire connections, a wireless link or router, or an intranet. In some embodiments, the remote devices 102 and 112 and the host device 122 may be communicatively coupled using a combination of one or more networks and/or one or more local connections. For example, the first remote device 102 may be hardwired to the host device 122 (e.g., connected with an Ethernet cable) while the second remote device 112 may communicate with the host device using the network 150 (e.g., over the Internet).

In some embodiments, the network 150 can be implemented within a cloud computing environment, or using one or more cloud computing services. Consistent with various embodiments, a cloud computing environment may include a network-based, distributed data processing system that provides one or more cloud computing services. Further, a cloud computing environment may include many computers (e.g., hundreds or thousands of computers or more) disposed within one or more data centers and configured to share resources over the network 150.

In some embodiments, the remote devices 102 and 112 may enable users to submit (or may submit automatically with or without user input) electronic documents (e.g., medical reports and medical images) to the host devices 122 in order to identify potential problems in the medical report. For example, the remote devices 102 and 112 may include electronic document submission modules 110 and 120 and a user interface (UI). The electronic document submission modules 110 and 120 may be in the form of a web browser or any other suitable software module, and the UI may be any type of interface (e.g., command line prompts, menu screens, graphical user interfaces). The UI may allow a user to interact with the remote devices 102 and 112 to submit, using the document submission modules 110 and 120, medical data (including medical reports and medical images) to the host device 122.

In some embodiments, the host device 122 may include a natural language processing system 132. The natural language processing system 132 may include a natural language processor 134, a search application 136, and a report analysis module 138. The natural language processor 134 may include numerous subcomponents, such as a tokenizer, a part-of-speech (POS) tagger, a semantic relationship identifier, and a syntactic relationship identifier. An example natural language processor is discussed in more detail in reference to FIG. 2.

The search application 136 may be implemented using a conventional or other search engine, and may be distributed across multiple computer systems. The search application 136 may be configured to search one or more databases or other computer systems for content that is related to an electronic document (such as a medical report) submitted by a remote device 102. For example, the search application 136 may be configured to search medical dictionaries, papers, and/or archived medical reports to help identify a condition, and criteria associated with the condition, in the received medical report. The report analysis module 138 may be configured to analyze a medical report to identify a condition (e.g., bone fracture, tumor, internal bleeding) and a criterion (e.g., the size of the fracture or tumor). The report analysis module 138 may include one or more modules or units, and may utilize the search application 136, to perform its functions (e.g., to determine a condition and a criterion), as discussed in more detail in reference to FIG. 2.

In some embodiments, the host device 122 may include an image processing system 142. The image processing system 142 may be configured to analyze medical images (e.g., X-Ray images, CAT scan images) to create an image analysis. The image analysis may include an image condition and an image criterion present in the medical images as determined by the image processing system 142. The image processing system 142 may utilize one or more models, modules, or units to perform its functions (e.g., to analyze the medical image and generate an image analysis). For example, the image processing system 142 may include one or more image processing models that are configured to identify specific conditions and criteria in a medical image. The image processing models may include a fracture analysis model 144 to analyze X-Ray images to identify the presence, size, type, and location of bone fractures. As another example, the image processing system 142 may include a tumor analysis model 146 to identify the size and location of tumors from a CAT scan or a positron emission topography (PET) scan image. In some embodiments, the image processing models may be implemented as software modules. For example, the image processing system 142 may include a fracture analysis module and a tumor analysis module. In some embodiments, a single software module may be configured to analyze the image(s) using the image processing models.

In some embodiments, the image processing system 142 may include a condition receiving module 148. The condition receiving module 148 may be configured to receive, from the natural language processing system, a condition which has been determined by analyzing a medical report. The condition receiving module 148 may then determine which modules within the image processing system 142 (e.g., the fracture analysis module 144 and the tumor analysis module 146) should be used to analyze the received medical image. For example, the natural language processing system 132 may identify, from a medical report, that a patient has been diagnosed with a bone fracture in his tibia. The medical report may be accompanied by an X-Ray image of the patient's lower leg, including the tibia. Accordingly, the condition receiving module 148 may determine that the image analysis should be generated using the fracture analysis module 144, instead of, e.g., the tumor analysis module 146.

In some embodiments, the host device 122 may include a comparator 130. The comparator 130 may be configured to receive a condition and a criterion from the natural language processing system 132 and an image analysis from the image processing system 142. The comparator 130 may be further configured to compare the image analysis to the condition and to the criterion to determine whether there is a potential problem with the medical report. In response to determining that the report contains an error, the comparator may be configured to notify the remote device 102 or 112 that transmitted the medical data to the host device 122.

In some embodiments, the host device may have an optical character recognition (OCR) module. The OCR module may be configured to receive a medical report sent from the remote devices 102 and 112 and perform optical character recognition (or a related process) on the medical report to convert it into machine-encoded text so that the natural language processing system 132 may perform NLP on the report. For example, the first remote device 102 may transmit an image of a scanned medical report to the host device. The OCR module may convert the image into machine-encoded text, and then the converted report may be sent to the natural language processing system 132 for analysis. In some embodiments, the OCR module may be a subcomponent of the natural language processing system 132. In other embodiments, the OCR module may be a standalone module within the host device 122. In still other embodiments, the OCR module may be located on the remote devices 102 and 112 and may perform OCR on the medical reports before they are sent to the host device 122.

While FIG. 1 illustrates a computing environment 100 with a single host device 122 and two remote devices 102 and 112, suitable computing environments for implementing embodiments of this disclosure may include any number of remote devices and host devices. The various models, modules, systems, and components illustrated in FIG. 1 may exist, if at all, across a plurality of host devices and remote devices. For example, some embodiments may include two host devices. The two host devices may be communicatively coupled using any suitable communications connection (e.g., using a WAN, a LAN, a wired connection, an intranet, or the Internet). The first host device may include a natural language processing system configured to receive and analyze a medical report, and the second host device may include an image processing system configured to receive and analyze a medical image, such as an X-Ray image or a computerized axial tomography scan (CAT scan) image, to generate an image analysis.

It is noted that FIG. 1 is intended to depict the representative major components of an exemplary computing environment 100. In some embodiments, however, individual components may have greater or lesser complexity than as represented in FIG. 1, components other than or in addition to those shown in FIG. 1 may be present, and the number, type, and configuration of such components may vary.

Figure 2:
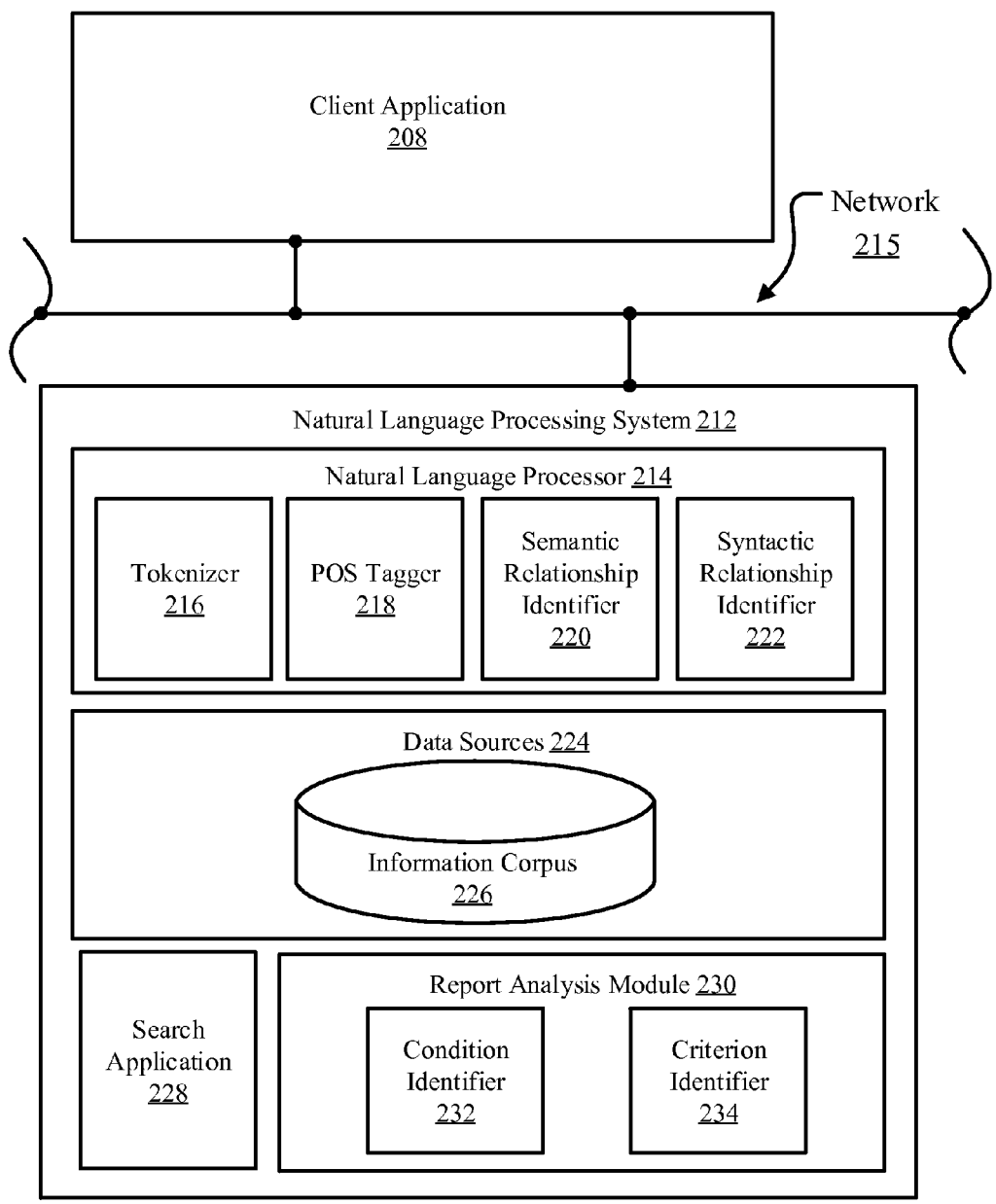
FIG. 2 illustrates a block diagram of an example natural language processing system configured to analyze a medical report to identify a condition and a criterion, in accordance with embodiments of the present disclosure.

Referring now to FIG. 2, shown is a block diagram of an exemplary system architecture 200, including a natural language processing system 212, configured to analyze medical data to identify a condition and a criterion, in accordance with embodiments of the present disclosure. In some embodiments, a remote device (such as remote device 102 of FIG. 1) may submit electronic documents (such as medical reports) to be analyzed to the natural language processing system 212 which may be housed on a host device (such as host device 122 of FIG. 1). Such a remote device may include a client application 208, which may itself involve one or more entities operable to generate or modify information in the medical report that is then dispatched to a natural language processing system 212 via a network 215.

Consistent with various embodiments, the natural language processing system 212 may respond to electronic document submissions sent by a client application 208. Specifically, the natural language processing system 212 may analyze a received medical report to identify a patient's diagnosed condition and a criterion describing, e.g., the severity of the condition. In some embodiments, the natural language processing system 212 may include a natural language processor 214, data sources 224, a search application 228, and a report analysis module 230. The natural language processor 214 may be a computer module that analyzes the received medical reports and other electronic documents. The natural language processor 214 may perform various methods and techniques for analyzing electronic documents (e.g., syntactic analysis, semantic analysis, etc.). The natural language processor 214 may be configured to recognize and analyze any number of natural languages. In some embodiments, the natural language processor 214 may parse passages of the documents. Further, the natural language processor 214 may include various modules to perform analyses of electronic documents. These modules may include, but are not limited to, a tokenizer 216, a part-of-speech (POS) tagger 218, a semantic relationship identifier 220, and a syntactic relationship identifier 222.

In some embodiments, the tokenizer 216 may be a computer module that performs lexical analysis. The tokenizer 216 may convert a sequence of characters into a sequence of tokens. A token may be a string of characters included in an electronic document and categorized as a meaningful symbol. Further, in some embodiments, the tokenizer 216 may identify word boundaries in an electronic document and break any text passages within the document into their component text elements, such as words, multiword tokens, numbers, and punctuation marks. In some embodiments, the tokenizer 216 may receive a string of characters, identify the lexemes in the string, and categorize them into tokens.

Consistent with various embodiments, the POS tagger 218 may be a computer module that marks up a word in passages to correspond to a particular part of speech. The POS tagger 218 may read a passage or other text in natural language and assign a part of speech to each word or other token. The POS tagger 218 may determine the part of speech to which a word (or other text element) corresponds based on the definition of the word and the context of the word. The context of a word may be based on its relationship with adjacent and related words in a phrase, sentence, or paragraph. In some embodiments, the context of a word may be dependent on one or more previously analyzed electronic documents (e.g., the content of one medical report may shed light on the meaning of text elements in another medical report). Examples of parts of speech that may be assigned to words include, but are not limited to, nouns, verbs, adjectives, adverbs, and the like. Examples of other part of speech categories that POS tagger 218 may assign include, but are not limited to, comparative or superlative adverbs, wh-adverbs, conjunctions, determiners, negative particles, possessive markers, prepositions, wh-pronouns, and the like. In some embodiments, the POS tagger 218 may tag or otherwise annotate tokens of a passage with part of speech categories. In some embodiments, the POS tagger 218 may tag tokens or words of a passage to be parsed by the natural language processing system 212.

In some embodiments, the semantic relationship identifier 220 may be a computer module that may be configured to identify semantic relationships of recognized text elements (e.g., words, phrases) in documents. In some embodiments, the semantic relationship identifier 220 may determine functional dependencies between entities and other semantic relationships.

Consistent with various embodiments, the syntactic relationship identifier 222 may be a computer module that may be configured to identify syntactic relationships in a passage composed of tokens. The syntactic relationship identifier 222 may determine the grammatical structure of sentences such as, for example, which groups of words are associated as phrases and which word is the subject or object of a verb. The syntactic relationship identifier 222 may conform to formal grammar.

In some embodiments, the natural language processor 214 may be a computer module that may parse a document and generate corresponding data structures for one or more portions of the document. For example, in response to receiving a medical report at the natural language processing system 212, the natural language processor 214 may output parsed text elements from the medical report as data structures. In some embodiments, a parsed text element may be represented in the form of a parse tree or other graph structure. To generate the parsed text element, the natural language processor 214 may trigger computer modules 216-222.

In some embodiments, the output of natural language processor 214 may be used by search application 228 to perform a search of a set of (i.e., one or more) corpora to retrieve one or more conditions and one or more associated criteria to send to an image processing system and to a comparator. As used herein, a corpus may refer to one or more data sources, such as the data sources 224 of FIG. 2. In some embodiments, the data sources 224 may include data warehouses, information corpora, data models, and document repositories. In some embodiments, the data sources 224 may include an information corpus 226. The information corpus 226 may enable data storage and retrieval. In some embodiments, the information corpus 226 may be a storage mechanism that houses a standardized, consistent, clean, and integrated list of conditions. The information corpus 226 may also store, for each condition, a list of associated criteria. For example, the information corpus 226 may include the types of bone fractures (e.g., open, closed, transverse). The data may be sourced from various operational systems. Data stored in the information corpus 226 may be structured in a way to specifically address reporting and analytic requirements. In some embodiments, the information corpus 226 may be a relational database.

In some embodiments, the report analysis module 230 may be a computer module that identifies a condition and a criterion by analyzing a medical report. In some embodiments, the report analysis module 230 may include a condition identifier 232 and a criterion identifier 234. When a medical report is received by the natural language processing system 212, the report analysis module 230 may be configured to analyze the medical report using natural language processing to identify a condition. The report analysis module 230 may first parse the medical report using the natural language processor 214 and related subcomponents 216-222. After parsing the medical report, the condition identifier 232 may identify one or more conditions present in the medical report. This may be done by, e.g., searching a medical dictionary (e.g., information corpus 226) using the search application 228. Once a condition is identified, the condition identifier 232 may be configured to transmit the condition to an image processing system (shown in FIG. 1) and/or to a comparator (shown in FIG. 1).

The criterion identifier 234 may identify a criterion (e.g., the severity of the condition) in the medical report. This may be done by searching the medical report for known identifiers related to the condition. The known identifiers may be found by searching through a list of identifiers. For example, fractures are often described by their location, size, and type. Fractures may also be described by their "Gustilo grade" using the Gustilo open fracture classification system if they are open fractures. If the condition identifier 232 identifies a bone fracture as the condition, the criterion identifier 234 may search the medical report for identifying information relating to bone fractures to determine a criterion. Such identifying information may include words or phrases indicating length (e.g., 10 cm), words that describe types of fractures (e.g., open, closed, transverse, and spiral), and words and phrases identifying a fracture's Gustilo grade (e.g., Grade IIIB) In order to identify criteria associated with the identified condition, the criterion identifier 234 may search the information corpus 226 using the search application 228 to receive a list of criteria often associated with the identified condition. In some embodiments, the list of criteria may be predetermined. In some embodiments, the computer system may generate the list by analyzing a plurality of medical reports. The criterion identifier 234 may then search, using natural language processing, the medical report for the list of criteria. After identifying a criterion relating to the condition, the criterion identifier 234 may be configured to transmit the criterion to an image processing system and/or to a comparator (both shown in FIG. 1)

Figure 3:
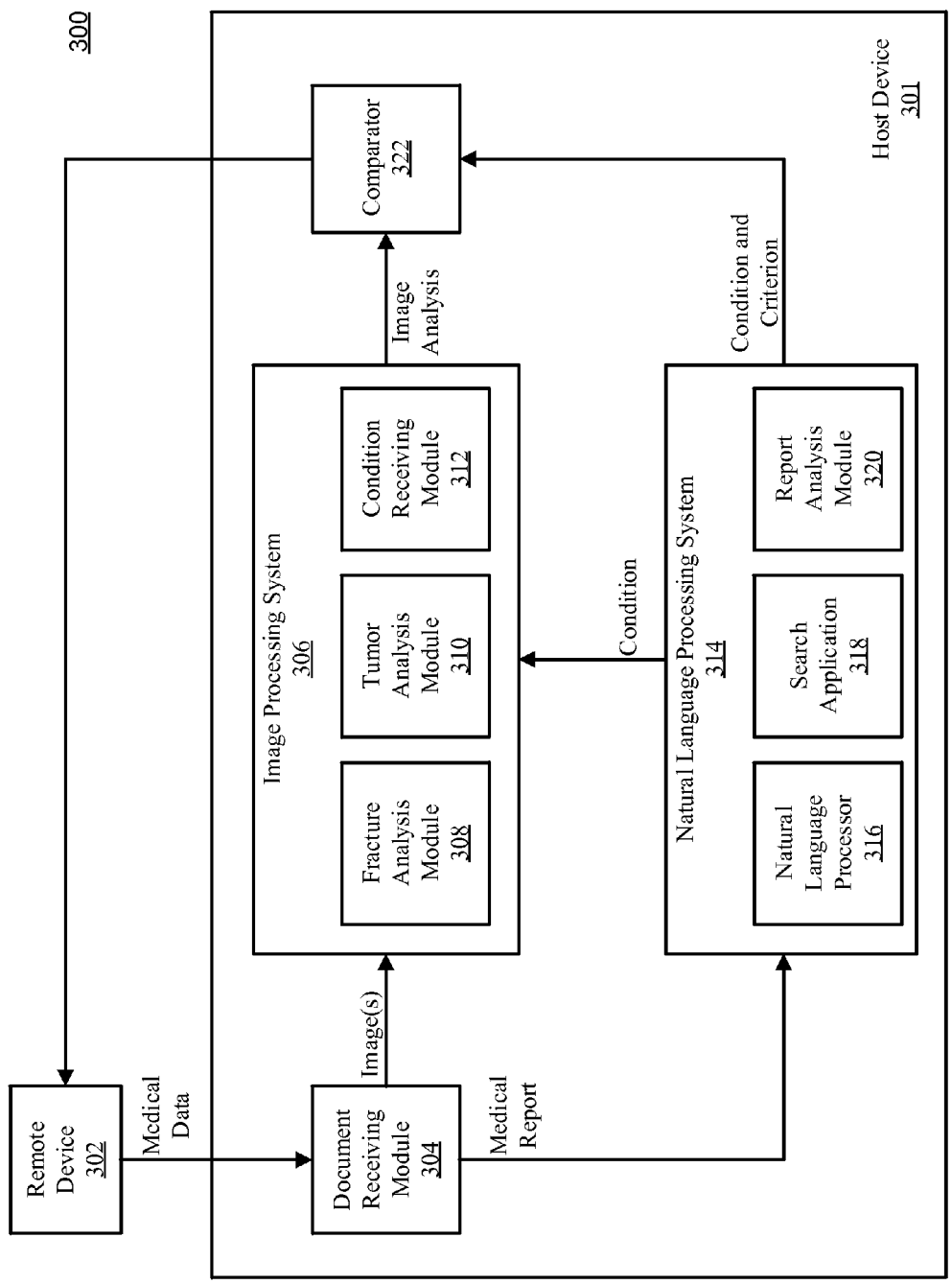
FIG. 3 illustrates a block diagram of an example high level logical architecture of a system for identifying errors in medical data, in accordance with embodiments of the present disclosure.

Referring now to FIG. 3, shown is a block diagram of an example high level logical architecture of a system 300 for identifying errors in medical data, in accordance with embodiments of the present disclosure. In some embodiment, the host device 301 and the remote device 302 may include the same components as the host device 122 and remote devices 102 and 112 of FIG. 1, respectively. A remote device 302 may submit medical data to a document receiving module 304. The medical data may include one or more reports and one or more images, such as an X-Ray image. The document receiving module 304 may be configured to receive the medical data and to send image(s) to the image processing system 306 and report(s) to the natural language processing system 314.

In some embodiments, the natural language processing system 314 may include the same modules and components as the natural language processing system 212 (shown in FIG. 2). The natural language processing system 314 may include, e.g., a natural language processor 316, a search application 318, and a report analysis module 320. The natural language processing system 314 may be configured to analyze the medical report to identify one or more conditions and one or more criteria relating to the severity of each condition. After identifying a condition and a criterion, the natural language processing system 314 may transmit the condition to the image processing system 306. The natural language processing system 314 may also transmit both the condition and the criterion to a comparator 322.

In some embodiments, the image processing system 306 may include the same modules and components as the image processing system 142 (shown in FIG. 1). The image processing system 306 may include, e.g., a fracture analysis module 308, a tumor analysis module 310, and a condition receiving module 312. The condition receiving module 312 may be configured to receive, from the natural language processing system 314, an identified condition determined by analyzing one or more medical reports. Based on the identified condition, the condition receiving module 312 may determine which image processing module should analyze the image received from the document receiving module 304. For example, if the natural language processing system 314 reports that the condition is a tumor, the condition receiving module 312 may call on the tumor analysis module 310 to analyze the image(s).

In some embodiments, the image processing system 306 may have modules directed towards other conditions. For example, the image processing system 306 may have modules dedicated towards analyzing images to detect signs of diabetes, problems with the structure of a heart, torn ligaments, and/or bulging discs. Many targeted image analysis processes used to identify specific conditions from medical images are known to persons of ordinary skill in the art, and the present disclosure should not be limited to the particular examples described herein.

After the image processing system 306 has analyzed the received image(s) using an image processing module, it may transmit an image analysis to the comparator 322. The image analysis may include one or more image conditions and/or one or more image criteria identified in the image(s). In some embodiments, the image analysis may only include the image criterion identified by the image processing system 306. The comparator 322 may receive the image analysis and compare it to the condition and criterion received from the natural language processing system 314. In some embodiments, the comparator will determine whether the condition identified by the natural language processing system 314 and the image condition determined by the image processing system 306 match. If they do not match, the comparator may send a notification that there may be a potential problem with the medical report to the remote device 302.

If the identified condition matches the image condition, the comparator may compare the criterion identified by the natural language processing system 314 to the image criterion. If the difference between the criterion and the image criterion is within a threshold, the comparator may determine that the report is accurate. For example, the natural language processing system 314 may indicate that a bone fracture (condition) is 7 cm long (criterion). The image analysis may indicate that bone fracture is actually 9 cm long (image criterion). If the comparator is configured to use a 3 cm threshold, it may determine that there is no potential problem with the medical report. If the difference between the identified criterion and the image criterion is larger than the threshold, the comparator may send a notification that there may be a potential problem with the medical report to the remote device 302.

Figure 4:
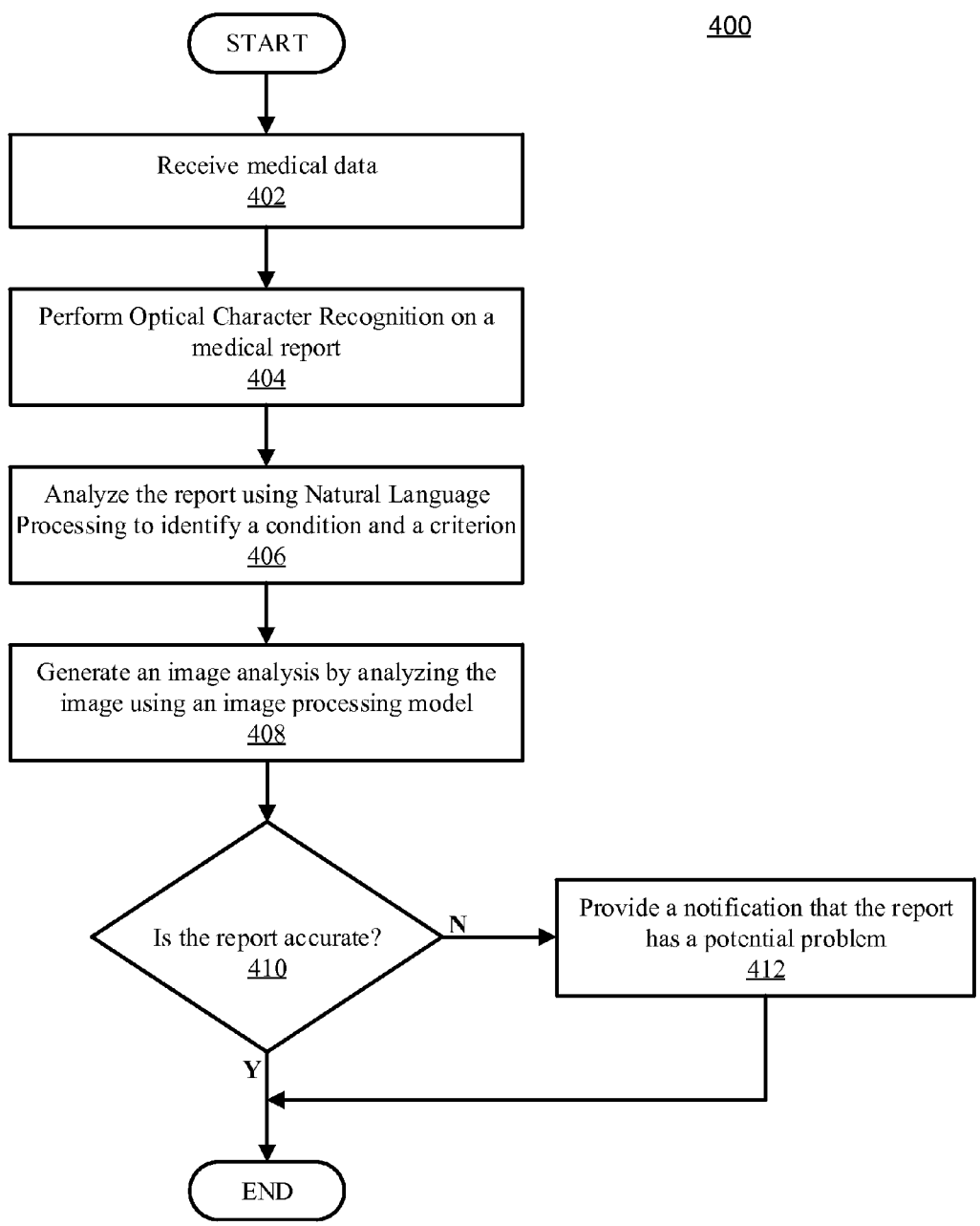
FIG. 4 illustrates a method for identifying errors in medical data using natural language processing and image analysis, in accordance with embodiments of the present disclosure.

Referring now to FIG. 4, shown is a method 400 for identifying errors in medical data using natural language processing and image analysis, in accordance with embodiments of the present disclosure. In some embodiments, the method 400 may be performed by one or more computer systems. The method 400 may begin at operation 402, where a computer system may receive medical data. The medical data may include one or more reports (e.g., a doctor's medical reports) and one or more images. In some embodiments, the medical data may include video and/or clinical write ups (e.g., lab reports). After receiving the medical data at operation 402, the computer system may perform optical character recognition (OCR) on the medical report to convert the report into machine-encoded text at operation 404. In some embodiments, the computer system may perform optical word recognition, intelligent character recognition (ICR), or intelligent word recognition (IWR) instead of, or in combination with, the OCR at operation 404.

Optical word recognition, like optical character recognition, is often used to convert typewritten text to machine-encoded text. Optical word recognition focuses on words (instead of individual characters) when converting to machine-encoded text. ICR and IWR are related technologies that are primarily used to convert handwritten printscript and/or cursive text into machine-encoded text. ICR converts the handwritten printscript one character or glyph at a time, whereas IWR converts the handwritten printscript one word at a time.

In some embodiments, the received medical report may already be in machine-encoded text, and operation 404 may be skipped. Once the medical report is in machine-encoded text, the computer system may analyze the medical report using natural language processing (NLP) to identify a condition and a criterion at operation 406. The identified condition may be a condition that a doctor diagnosed in a patient. For example, the condition may be a bone fracture, a torn ligament, a tumor, or a type of cancer. The criterion may indicate the severity or other distinguishing characteristic about the condition. For example, if the condition is a bone fracture, the criterion may describe the type of fracture (e.g., open, closed, transverse, etc.) and/or the size of the fracture (e.g., 10 cm).

Natural language processing, as discussed herein, may incorporate any relevant natural processing techniques including, without limitation, those techniques discussed in reference to modules 216-222 of FIG. 2. For example, in embodiments, the natural language processing technique may include analyzing syntactic and semantic content in the report. The natural language processing technique may be configured to parse structured data (e.g., tables, graphs) and unstructured data (e.g., textual content containing words, numbers). In certain embodiments, the natural language processing technique may be embodied in a software tool or other program configured to analyze and identify the semantic and syntactic elements and relationships present in the report. More particularly, the natural language processing technique can include parsing the grammatical constituents, parts of speech, context, and other relationships (e.g., modifiers) of the medical report. The natural language processing technique can be configured to recognize keywords, contextual information, and metadata tags associated with words, phrases, or sentences related to a condition and criterion. The syntactic and semantic elements can include information such as word frequency, word meanings, text font, italics, hyperlinks, proper names, noun phrases, parts-of-speech, or the context of surrounding words. Other syntactic and semantic elements are also possible.

After identifying a condition and a criterion at operation 406, the method 400 may progress to operation 408, where the computer system may generate an image analysis by analyzing the image using an image processing model. The image analysis may include an image criterion and/or an image condition that has been determined, by the computer system, to be present in the image. In some embodiments, an image processing system may analyze the image using one or more specialized modules, as discussed herein. The image processing system may determine which image processing module to use by receiving, from a natural language processing system, an identified condition and choosing the module most appropriate for that condition. For example, the computer system may have a first module dedicated to analyzing images to detect the presence and size of bone fractures and a second module to detect the presence and size of tumors. If the condition determined by analyzing the medical report indicates that there is a tumor, the module for detecting tumors may be executed.

After generating the image analysis at operation 408, the computer system may determine whether the report is accurate at decision block 410. To determine whether the report is accurate, the computer system may compare the criterion to the image analysis. If the image analysis matches the criterion, the computer system may determine that the report is accurate (i.e., has no identified potential problems). In some embodiments, the criterion may be a descriptive word. For example, if the condition is a fracture, the criterion may indicate that the fracture is an "open" fracture. In other embodiments, the criterion may be a number, with or without dimensions, such as the length of a fracture or a grade of a fracture. For example, the criterion determined by analyzing the report might indicate that the fracture is 10 cm long. In these embodiments, the computer system may determine that the image analysis and the criterion match when the difference between them is less than a threshold.

If the criterion and the image analysis match, the computer system may determine that the report is accurate and the method 400 may end. If the criterion and the image analysis do not match, the computer system may determine that the report is not accurate and it may provide a notification that the report has a potential problem at operation 412. In some embodiments, the notification may be transmitted by the computer system to a remote computer system to alert a user that there is a potential problem with the report. After that computer system provides a notification that the report has a potential problem to a user, the method 400 may end.

As discussed in more detail herein, it is contemplated that some or all of the operations of some of the embodiments of methods described herein may be performed in alternative orders or may not be performed at all; furthermore, multiple operations may occur at the same time or as an internal part of a larger process.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the various embodiments. As used herein, the singular forms "a," "an," and "the" are intended to include the plural forms as well, unless the context clearly indicates otherwise. It will be further understood that the terms "includes" and/or "including," when used in this specification, specify the presence of the stated features, integers, steps, operations, elements, and/or components, but do not preclude the presence or addition of one or more other features, integers, steps, operations, elements, components, and/or groups thereof. In the previous detailed description of exemplary embodiments of the various embodiments, reference was made to the accompanying drawings (where like numbers represent like elements), which form a part hereof, and in which is shown by way of illustration specific exemplary embodiments in which the various embodiments may be practiced. These embodiments were described in sufficient detail to enable those skilled in the art to practice the embodiments, but other embodiments may be used and logical, mechanical, electrical, and other changes may be made without departing from the scope of the various embodiments. In the previous description, numerous specific details were set forth to provide a thorough understanding the various embodiments. But, the various embodiments may be practiced without these specific details. In other instances, well-known circuits, structures, and techniques have not been shown in detail in order not to obscure embodiments.

Different instances of the word "embodiment" as used within this specification do not necessarily refer to the same embodiment, but they may. Any data and data structures illustrated or described herein are examples only, and in other embodiments, different amounts of data, types of data, fields, numbers and types of fields, field names, numbers and types of rows, records, entries, or organizations of data may be used. In addition, any data may be combined with logic, so that a separate data structure may not be necessary. The previous detailed description is, therefore, not to be taken in a limiting sense.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present invention has been described in terms of specific embodiments, it is anticipated that alterations and modification thereof will become apparent to the skilled in the art. Therefore, it is intended that the following claims be interpreted as covering all such alterations and modifications as fall within the true spirit and scope of the invention.

What is claimed is:

1. A computer implemented method for identifying errors in medical data, the method comprising:
   receiving medical data comprising a report and an image;
   analyzing the report, by a processor, using natural language processing (NLP) to identify a condition and a criterion, wherein the condition is a medical condition, and wherein the criterion includes diagnostic information that corresponds to the condition;
   generating an image analysis, by the processor, by analyzing the image using an image processing model; and
   determining whether the report has a potential problem by comparing at least the criterion to the image analysis.

2. The method of claim 1, wherein there are a plurality of image processing models, each image processing model of the plurality of image processing models corresponding to a group of medical conditions, and wherein the image processing model used to generate the image analysis is selected based on the condition.

3. The method of claim 1, the method further comprising:
   providing, in response to determining that the report has a potential problem, a notification indicating the potential problem.

4. The method of claim 1, wherein the report has a potential problem due to an optical character recognition (OCR) error.

5. The method of claim 1, wherein the report has a potential problem due to an optical word recognition error.

6. The method of claim 1, the method further comprising performing, prior to analyzing the report using natural language processing, optical character recognition on the report.

7. The method of claim 2, wherein the plurality of image processing models includes a fracture analysis model and a tumor analysis model.

8. The method of claim 7, wherein the fracture analysis model is configured to analyze X-Ray images to identify a presence, size, type, and location of bone fractures, and wherein the tumor analysis model is configured to analyze computerized axial tomography (CAT) scan images to identify the size and location of tumors.

9. The method of claim 7, wherein the plurality of image processing models further include a model for detecting signs of diabetes, a model for detecting problems with the structure of a heart, a model for detecting torn ligaments, and a model for detecting bulging discs.

10. The method of claim 1, wherein the image analysis includes an image condition and an image criterion, wherein the image condition is a medical condition identified in the image, and the image criterion is diagnostic information about the image condition.

11. The method of claim 10, wherein determining whether the report has a potential problem includes comparing the condition to the image condition and the criterion to the image criterion.

12. The method of claim 1, wherein the criterion includes a severity of the condition.

13. The method of claim 1, wherein the condition is a bone fracture, and wherein the criterion is a Gustilo grade of the bone fracture.

14. The method of claim 1, the method further comprising:
   transmitting, in response to determining that the report contains a potential problem, a notification and the report to a user.

15. The method of claim 1, wherein the condition is a bone fracture, wherein the criterion is a size of the bone fracture in the report, wherein the image analysis includes a size of the bone fracture identified in the image, and wherein the determining whether the report has a potential problem includes:
   determining a difference between the size of the bone fracture identified from the report and a size of the bone fracture identified in the image;
   comparing the difference to a threshold;
   determining that the difference is greater than the threshold; and
   determining, based on the difference being greater than the threshold, that the report has a potential problem.

16. The method of claim 1, the method further comprising:
   converting, prior to the analyzing the report using natural language processing, the report into machine-encoded text using optical character recognition.

17. A computer implemented method for identifying errors in medical data, the method comprising:
   receiving medical data of a patient, the medical data comprising a medical report and an image;
   converting the report into machine-encoded text using optical character recognition;
   analyzing, by a processor, the converted report using natural language processing (NLP) to identify a condition and a criterion, wherein the condition is a medical condition, and wherein the criterion includes a severity that corresponds to the condition;
   determining, based on the identified condition and from a plurality of image processing models, a particular image processing model that corresponds to the identified condition, wherein the plurality of image processing models includes a fracture analysis model and a tumor analysis model;
   generating, by the processor, an image analysis by analyzing the image using the particular image processing model, the image analysis including a an image condition and an image criterion, wherein the image condition is a medical condition identified in the image, and the image criterion is a severity of the image condition;
   determining that the condition and the image condition match;
   comparing, in response to determining that the condition and the image condition match, the criterion to the image criterion;
   determining that the criterion and the image criterion do not match; and
   transmitting, in response to determining that the criterion and the image criterion do not match, a notification that the report has a potential problem along with the report to a user.

* * * * *